(12) United States Patent
Sato (10) Patent No.: US 8,401,603 B2
(45) Date of Patent: *Mar. 19, 2013

(54) IMAGING DEVICE, METHOD THEREOF, AND PROGRAM

(75) Inventor: Hideo Sato, Tokyo (JP)

(73) Assignee: Sony Corporation, Tokyo (JP)

( * ) Notice: Subject to any disclaimer, the term of this patent is extended or adjusted under 35 U.S.C. 154(b) by 177 days.

This patent is subject to a terminal disclaimer.

(21) Appl. No.: 12/891,947

(22) Filed: Sep. 28, 2010

(65) Prior Publication Data

US 2011/0015506 A1  Jan. 20, 2011

Related U.S. Application Data

(63) Continuation of application No. 10/546,038, filed as application No. PCT/JP2004/019715 on Dec. 22, 2004, now Pat. No. 7,840,258.

(30) Foreign Application Priority Data

Dec. 24, 2003 (JP) .................... 2003-428406

(51) Int. Cl.
 *A61B 5/00* (2006.01)
 *A61B 6/00* (2006.01)
(52) U.S. Cl. ........................ 600/310; 600/476
(58) Field of Classification Search .............. 600/310, 600/476
 See application file for complete search history.

(56) References Cited

U.S. PATENT DOCUMENTS

| 4,704,633 A | 11/1987 | Matsumoto |
| 5,185,808 A * | 2/1993 | Cok ............................. 382/284 |
| 5,757,343 A * | 5/1998 | Nagakubo ...................... 345/63 |
| 2002/0183624 A1 * | 12/2002 | Rowe et al. ................... 600/476 |
| 2003/0139650 A1 | 7/2003 | Homma |

FOREIGN PATENT DOCUMENTS

| JP | 2003-087653 | 3/2003 |
| JP | 2003-187235 | 7/2003 |
| JP | 2003-242487 | 8/2003 |

OTHER PUBLICATIONS

International Search Report issued Apr. 12, 2005 in PCT/JP2004/19715 filed Aug. 17, 2005.

* cited by examiner

*Primary Examiner* — Tse Chen
*Assistant Examiner* — Hien Nguyen
(74) *Attorney, Agent, or Firm* — Oblon, Spivak, McClelland, Maier & Neustadt, L.L.P.

(57) ABSTRACT

To realize an imaging device, imaging method and program capable of improving image quality. This invention controls light sources so as to irradiate a body with irradiation light of a luminance level higher than that in the air arriving at the body, adjusts the imaging sensitivity of a solid imaging element for performing photoelectric conversion on pattern scattered light obtained through the inside of the body, and masks the luminance level deterioration region of a pattern image obtained from the solid imaging element to treat the masked image as an image to be composed with a reference image.

4 Claims, 11 Drawing Sheets

IMAGING DEVICE, METHOD THEREOF, AND PROGRAM

CROSS-REFERENCE TO RELATED APPLICATIONS

This is a continuation of U.S. application Ser. No. 10/546,038, filed Jan. 6, 2006, which is a continuation of PCT/JP2004/19715, filed Dec. 22, 2004. This application is based upon and claims the benefit of priority from the prior Japanese Patent Application No. 2003-428406 filed Dec. 24, 2003. The entire contents of each of these documents are incorporated herein by reference.

TECHNICAL FIELD

This invention relates to an imaging device, method, and program and is suitably applied to a case of imaging blood vessels, for example.

BACKGROUND ART

Figure 11:
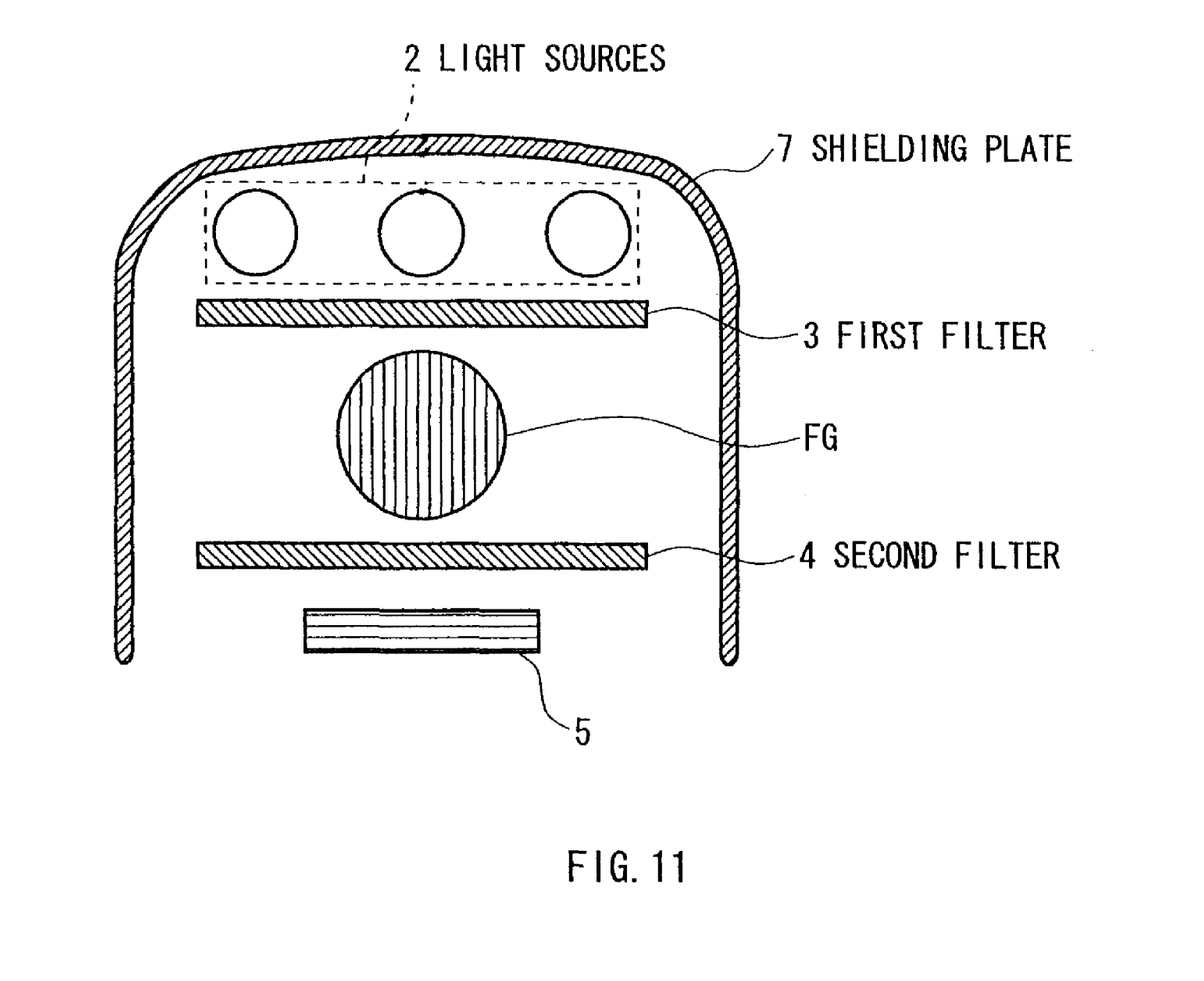
FIG. 11 is a schematic diagram showing a construction of a conventional imaging device.

Recently, a blood vessel formation pattern of blood vessels of a body has been attracted as one of unique body characteristics. As a device for imaging the blood vessel formation pattern, an imaging device 1 as shown in FIG. 11 has been proposed, for example.

This imaging device 1 has laser light sources 2 for emitting near-infrared light. On the light path of the near-infrared light emitted from the laser light sources 2, a first filter 3 for allowing light of specific near-infrared light bandwidth out of the near-infrared light to pass therethrough, a second filter 4 for allowing light of near-infrared light bandwidth which is absorbed in hemoglobin in blood vessels, out of light obtained through the first filter 3, and an imaging element 5 are arranged in order.

In this case, the imaging device 1 emits near-infrared light from the light sources 2 in a situation where, for example, a finger FG of a body is inserted between the first filter 3 and the second filter 4, resulting in irradiating the finger FG with the light through the first filter 3. Since this near-infrared light is specifically absorbed in instinct hemoglobin of blood vessel tissues inside the finger FG, scattered light obtained though the finger FG enters the imaging element 5 through the second filter 4 as blood vessel pattern light representing a formation pattern of the blood vessel tissues.

The imaging element 5 performs photoelectric conversion on the blood vessel pattern light with a plurality of photoelectric conversion elements that is arranged in a matrix in correspondence with pixels, in order to treat a signal obtained by the photoelectric conversion elements as a blood vessel image signal.

In this case, the imaging device 1 is provided with a physical shielding unit 7 for covering not only all units 2 to 5 existing on the light path of near-infrared light emitted from the light sources 2 but also the finger FG, so as to eliminates influence of light (hereinafter, referred to as outside light) in the air arriving at the finger FG on the near-infrared light. This, however, arises a large scale problem due to the shielding unit 7.

To solve this problem, such an imaging device has been proposed by the applicant of this invention that irradiates, for example, a finger with irradiation light of a luminance level higher than that of light in the air arriving at a body, performs photoelectric conversion on blood vessel pattern light obtained through the finger, with a solid imaging element, and adjusts imaging sensitivity of the solid imaging element by limiting the amount of the resultant signal per unit time (for example, refer to patent reference 1).

Since this imaging device can relatively reduce the amount of signal being accumulated in the solid imaging element as a result of the photoelectric conversion of the blood vessel pattern light and the outside light arriving at this time, imaging can be performed without physically blocking the irradiation route of the irradiation light and the finger and without substantive influence of the outside light on the imaging sensitivity of the solid imaging element to the blood vessel pattern light.

Patent Reference 1 Japanese Patent Application NO. 2003-371022

The imaging device, however, has a drawback in which an uneven blood vessel image is created because the reflex pathway of near-infrared light varies in a body due to the positions of the light sources and individuals and thus the solid imaging element cannot perform the photoelectric conversion on uniform blood vessel pattern light.

DISCLOSURE OF THE INVENTION

This invention has been made in view of foregoing and intends to propose a communication terminal device capable of simply realizing actual use of an imaging device and method capable of improving image quality.

To solve the above problem, this invention provides an imaging device with: a light source control means for controlling light sources so as to irradiate a body with irradiation light of a luminance level higher than that in the air arriving at the body; a sensitivity adjustment means for adjusting the imaging sensitivity of a solid imaging element for performing photoelectric conversion on pattern scattered light obtained through the inside of the body; and a masking means for masking the luminance level deterioration region of a pattern image obtained from the solid imaging element to treat the masked image as an image to be composed with a reference image.

Further, this invention provides a program causing a computer to execute an imaging method and process, with: a light source control step of controlling light sources so as to irradiate a body with irradiation light of a luminance level higher than that in the air arriving at the body; a sensitivity adjustment step of adjusting the imaging sensitivity of a solid imaging element for performing photoelectric conversion on pattern scattered light obtained through the inside of the body; and a masking step of masking a luminance level deterioration region of a pattern image obtained from the solid imaging element to treat the masked image as an image to be composed with a reference image.

According to this invention, light sources are controlled so as to irradiate a body with irradiation light of a luminance level higher than that in the air arriving at the body, the imaging sensitivity of a solid imaging element for performing photoelectric conversion on pattern scattered light obtained through the inside of the body is adjusted, and the luminance level deterioration region of a pattern image obtained from the solid imaging element is masked. As a result, even in a case where an image is created based on an uneven pattern scattered light which is obtained because there is a difference in reflex pathway of near-infrared light inside the body depending on the positions of the light sources and individuals, the unevenness of the image can be masked to use the image as an image to be composed with a reference image. Therefore, an even image representing the inside of the body can be obtained regardless of the positions of the light sources and individuals, thus making it possible to realize an imaging device, and an imaging method and program capable of improving image quality.

BEST MODE FOR CARRYING OUT THE INVENTION

One embodiment to which this invention is applied will be described in detail with reference to the accompanying drawings.

(1) First Embodiment (1-1) Construction of Imaging Device

Figure 1:
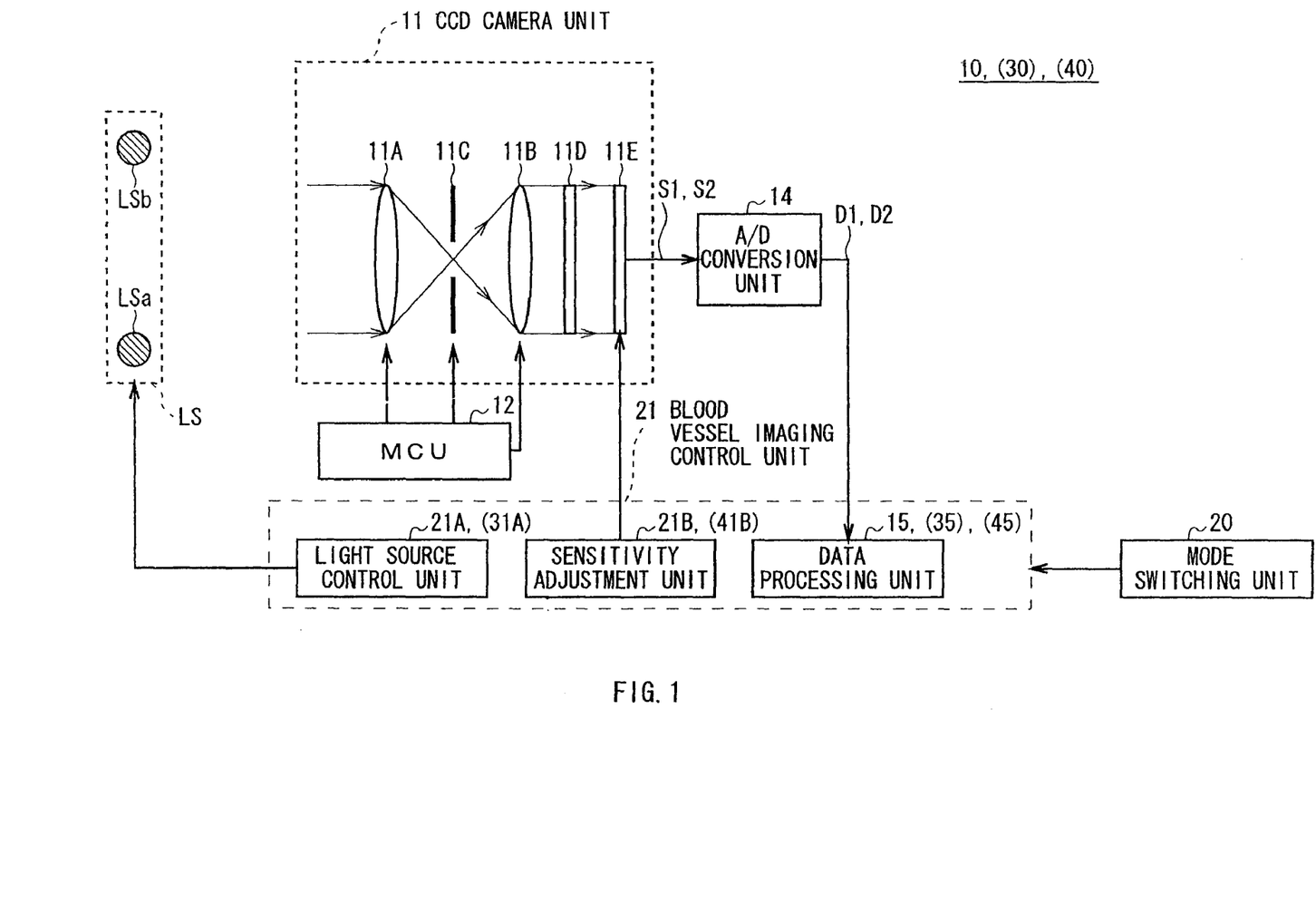
FIG. 1 is a schematic diagram showing a construction of an imaging device according to the first embodiment.

FIG. 1 shows an imaging device according to this embodiment. This imaging device 10 is designed to execute a mode (hereinafter, referred to as normal imaging mode) to image subjects such as bodies and backgrounds as imaging targets.

In this case, a CCD camera unit 11 guides the outside light in the air arriving from a front subject, to a CCD 11E via a lens 11A, an aperture 11C, a lens 11B, and an ultraviolet cut filter 11D in order. In this connection, the ultraviolet cut filter 11D comprises an RGB filter for allowing visible light and near-infrared light to pass therethrough.

At this time, an MCU (Micro Control Unit) 12 adjusts the amount of the outside light entering the CCD 11E by controlling an aperture value of the aperture 11C with an auto exposure control process and also adjusts a focus distance and a focus position by controlling the positions of the lens 11A and 11B with an auto focus control process.

Then the CCD 11E of the CCD camera unit 11 performs photoelectric conversion on the outside light arriving through the ultraviolet cut filter 11D, with a plurality of photoelectric conversion elements arranged in correspondence with pixels, reads charge signals being accumulated in the photoelectric conversion elements as a result of the photoelectric conversion, as an image signal S1 according to a readout clock supplied from a clock generator (not shown), and sends this to an A/D (Analog/Digital) conversion unit 14.

The A/D conversion unit 14 creates a digital image signal D1 by digitizing the image signal S1 and sends this to a data processing unit 15.

The data processing unit 14 stores and keeps the digital image signal D1 in, for example, an internal memory (not shown).

As described above, the imaging device 10 executes the normal imaging mode to image subjects such as bodies and backgrounds as imaging targets.

Figure 2:
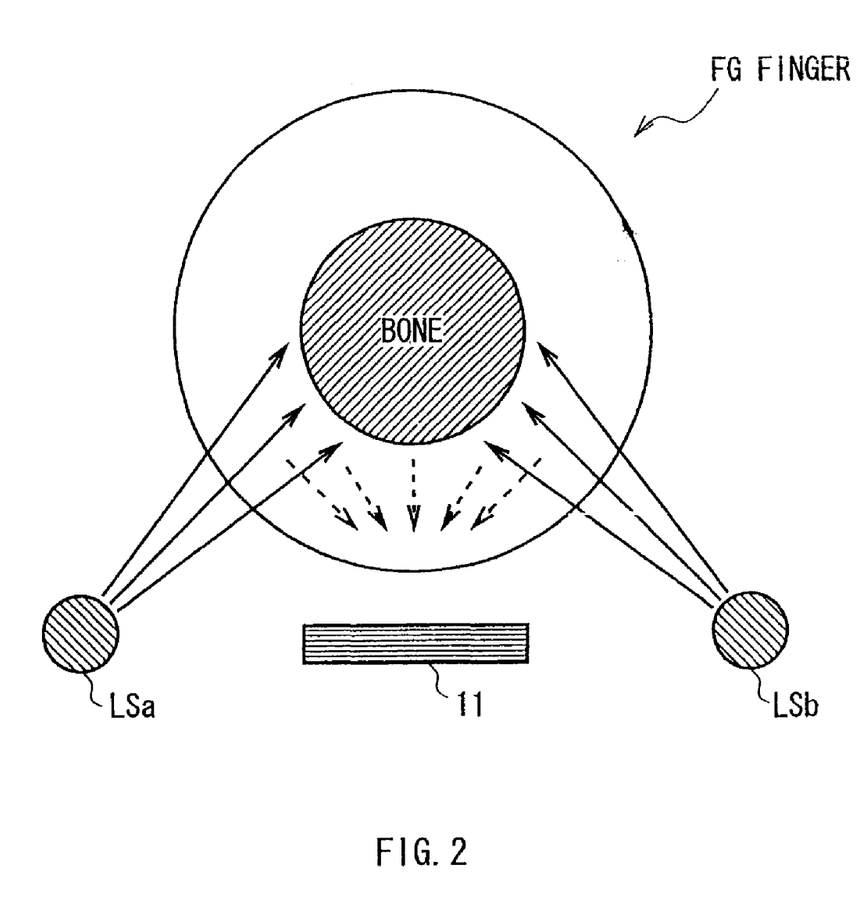
FIG. 2 is a schematic diagram showing the positions of near-infrared light sources and a light flow of near-infrared light.

In addition to the above units, as shown in FIG. 2, this imaging device 10 has two near-infrared light sources LS (LSa and LSb) for emitting near-infrared light toward the arrival direction of the outside light, in almost the same level as the position of the CCD camera unit 11, and is designed to execute a mode (hereinafter, referred to as a blood vessel imaging mode) to image blood vessel tissues inside a finger FG positioned in an irradiation direction, as an imaging target (hereinafter, referred to as specific imaging target).

In this case, when a prescribed blood vessel imaging command is entered via an operating unit (not shown), a mode switching unit 20 (FIG. 1) drives both a light source control unit 21A and a sensitivity adjustment unit 21B of a blood vessel imaging control unit 21.

The light source control unit 21A controls an output and so on, to the near-infrared light sources LS so as to have a preset value as a luminance level higher than that of the outside light which is normally obtained in the air, with the result that the near-infrared light sources LS irradiate the finger FG with near-infrared light of a luminance level higher than that of the outside light.

As shown in FIG. 2, this near-infrared light is specifically absorbed in the instinct hemoglobin of the blood vessel tissues (not shown) inside the finger FG, and passes through or is reflected by the other tissues. The outside light arriving at this time, on the other hand, is attenuated by being blocked by bones and becomes light which can be ignored because of near-infrared light of a higher luminance level.

In this case, near-infrared light obtained through the finger FG is guided to the CCD 11E via the lens 11A, the aperture 11C, the lens 11B, and the ultraviolet cut filter 11D shown in FIG. 1 in order, as blood vessel pattern light representing a formation pattern of blood vessel tissues. Then in each photoelectric conversion elements of the CCD 11E, a charge signal obtained as a result of the photoelectric conversion of the blood vessel pattern light is accumulated.

At this time, the sensitivity adjustment unit 21B adjusts the imaging sensitivity of the CCD 11E to the blood vessel pattern light by electrically limiting the amount of charge signal being accumulated in each photoelectric conversion elements of the CCD 11E with an exposure time control process called an electronic shutter.

Figure 3:
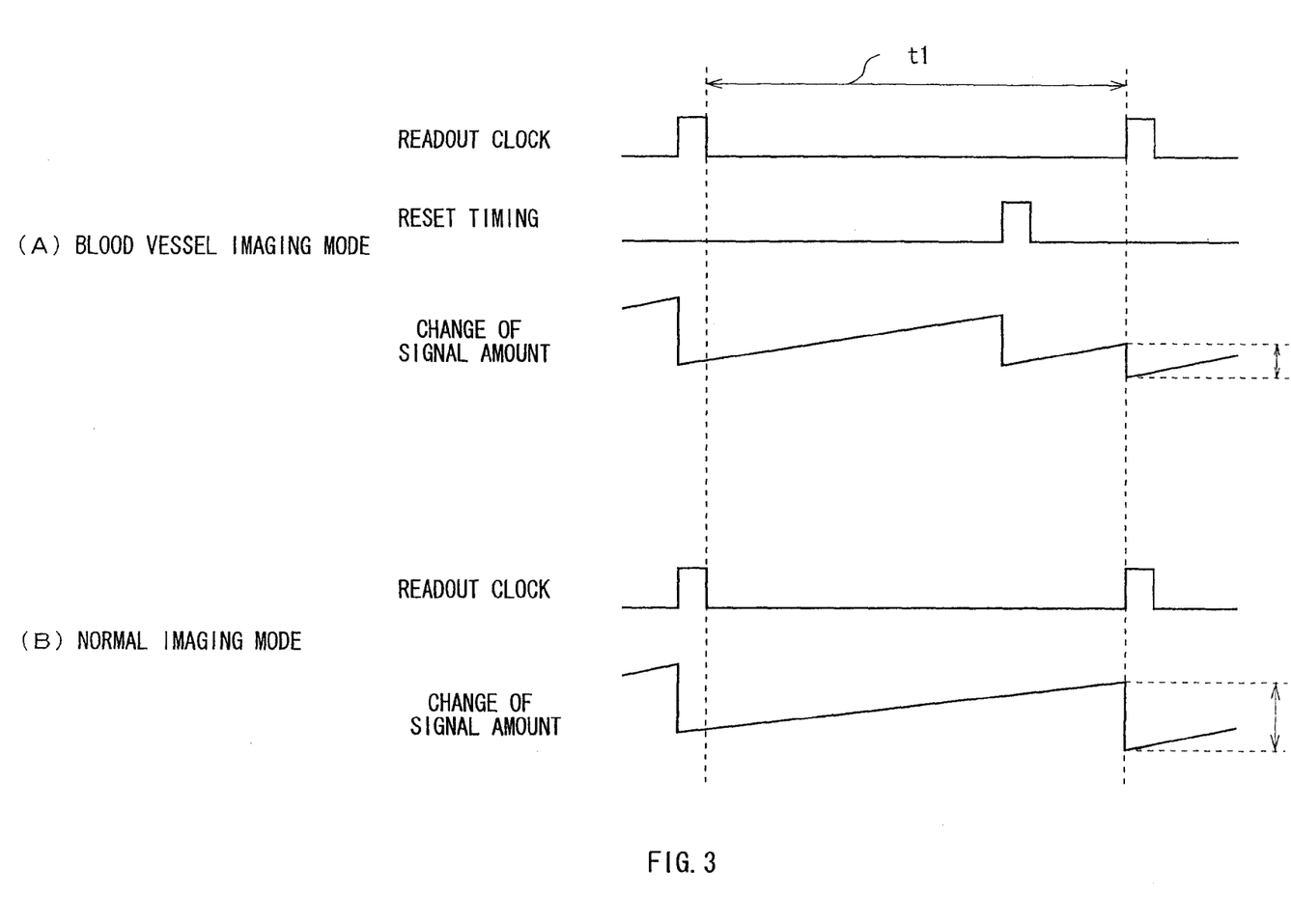
FIG. 3 is a schematic diagram explaining an electric shutter.

Specifically, as shown in FIG. 3, the sensitivity adjustment unit 21B performs resetting at prescribed reset timing within a period (hereinafter, referred to as charge accumulation period) t1 from rising of the readout clock to next rising which is next readout timing (FIG. 3(A)), so as to limit the amount of charge signal being accumulated in each photoelectric conversion element of the CCD 11E within the charge accumulation period t1 as compared with the amount of charge signal in the normal imaging mode (FIG. 3(B)) (FIG. 3(A)).

Figure 4:
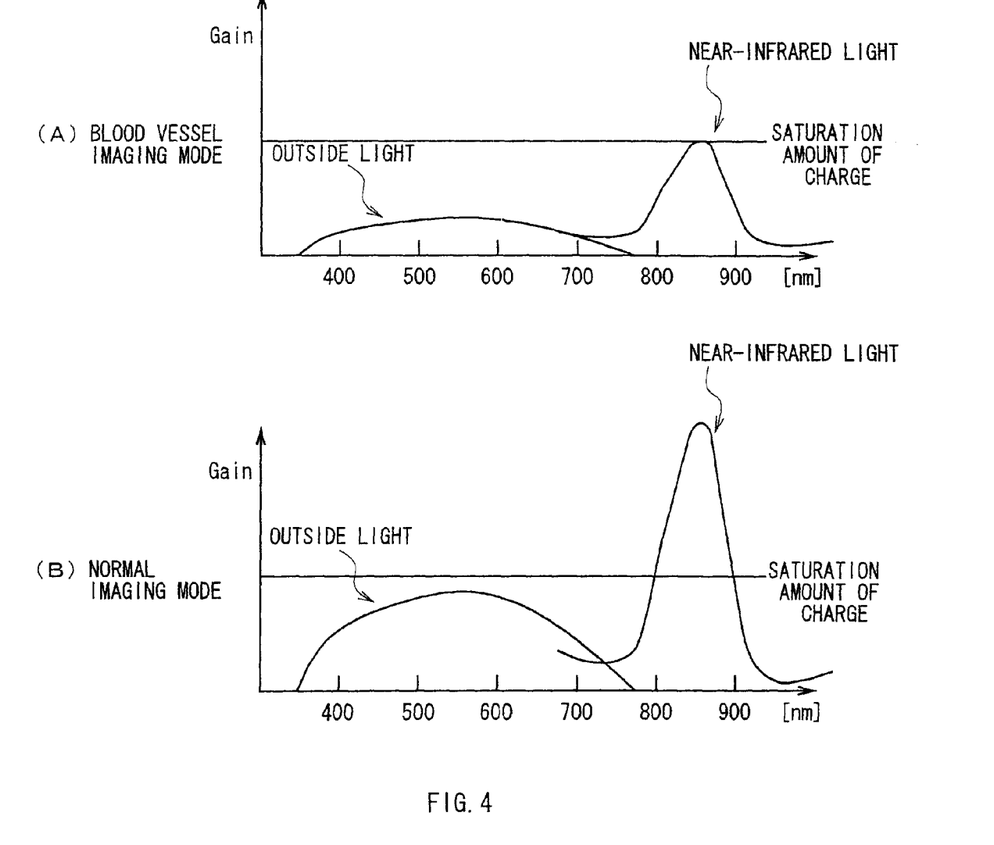
FIG. 4 is a schematic diagram explaining adjustment of imaging sensitivity of the electric shutter.

As a result, as shown in FIG. 4(A), the photoelectric conversion elements of the CCD 11E can previously prevent the charge signals being accumulated in the photoelectric conversion elements from being saturated within the charge accumulation period t1 (FIG. 4) due to the near-infrared light emitted from the near-infrared light sources LS has a higher luminance level than that of the outside light. Further, as shown in FIG. 4(B), the amount of charge signals being accumulated in the photoelectric conversion elements as a result of the photoelectric conversion of the blood vessel pattern light and the outside light arriving at this time are relatively reduced, so that the imaging sensitivity of the CCD 11E to the blood vessel pattern light is not affected by the outside light.

Then the CCD 11E reads the charge signals being accumulated after the amount of charge signal is limited with the exposure time control process of the sensitivity adjustment unit 21B, as a blood vessel image signal S2 (FIG. 1) at readout timing of the readout clock, and sends this to the A/D conversion unit 14. The A/D conversion unit 14 digitizes the blood vessel image signal S2 to create a digital blood vessel image signal D2 and sends this to the data processing unit 15.

The data processing unit 15 extracts a unique blood vessel formation pattern from the blood vessel image of the digital blood vessel image signal D2, and stores and keeps the extracted blood vessel formation pattern in an internal memory (not shown). In this case, the data processing unit 15 extracts a pattern representing an inside of a body, thereby being capable of preventing direct steal from a body as compared with a case of extracting a pattern of fingerprints or the like existing on the body surface and thus keeping the pattern as identification information with high confidentiality in the internal memory (not shown).

As described above, the imaging device 10 executes the blood vessel imaging mode and can perform imaging without physically blocking the irradiation route of near-infrared light and an imaging target and without substantial influence of the outside light on the imaging sensitivity of the CCD 11E to blood vessel pattern light.

In this case, the imaging device 10 drives the light source control unit 21A and the sensitivity adjustment unit 21B according to switching of the mode switching unit 20 to the blood vessel imaging mode out of the normal imaging mode and the blood vessel imaging mode, thereby being capable of reducing power consumed by the light source control unit 21A and using the CCD camera unit 11 for imaging both normal subjects and blood vessels.

In addition to the above configuration, by the light source control unit 21A of this imaging device 10, a finger FG is irradiated with light of wavelength including both wavelength which is specifically absorbed in oxygenation hemoglobin and wavelength which is specifically absorbed in deoxygenization hemoglobin out of hemoglobin (transport protein) of blood vessel tissues inside the finger FG, specifically, near-infrared light of wavelength from 700 [nm] to 900 [nm].

Thereby, the imaging device 10 can create a blood vessel image signal S2 faithfully representing capillary vessel tissues containing oxygenation and deoxygenization hemoglobin, with the CCD camera unit 11. In addition, in this case, since the wavelength is not strictly limited to one which is specifically absorbed in oxygenation and deoxygenization hemoglobin, not only hemoglobin can be previously prevented from varying due to concentration of energy on blood vessel tissues but also an S/N ratio can be improved and manufacturing can be simplified.

By the way, in the blood vessel imaging mode, the imaging device 10 emits near-infrared light of a luminance level higher than that of the outside light, toward an opposite side of the outside light entering the CCD 11E, from the near-infrared light sources LSa and LSb arranged in almost the same level as the CCD camera 11 (FIG. 2). Therefore, only by placing the finger FG in front of the CCD camera unit 11, the blood vessel image of the finger FG can be created as a digital blood vessel image signal D2 from blood vessel pattern light that is not substantially affected by the outside light arriving at this time.

In this case, however, blood vessel pattern light entering the CCD 11E through the finger FG becomes uneven light because the near-infrared light sources LSa and LSb existing near the finger FG emit near-infrared light of a luminance level higher than the outside light and the light amount of a part near the near-infrared light sources LSa and LSb is more than that of the other part.

Figure 5:
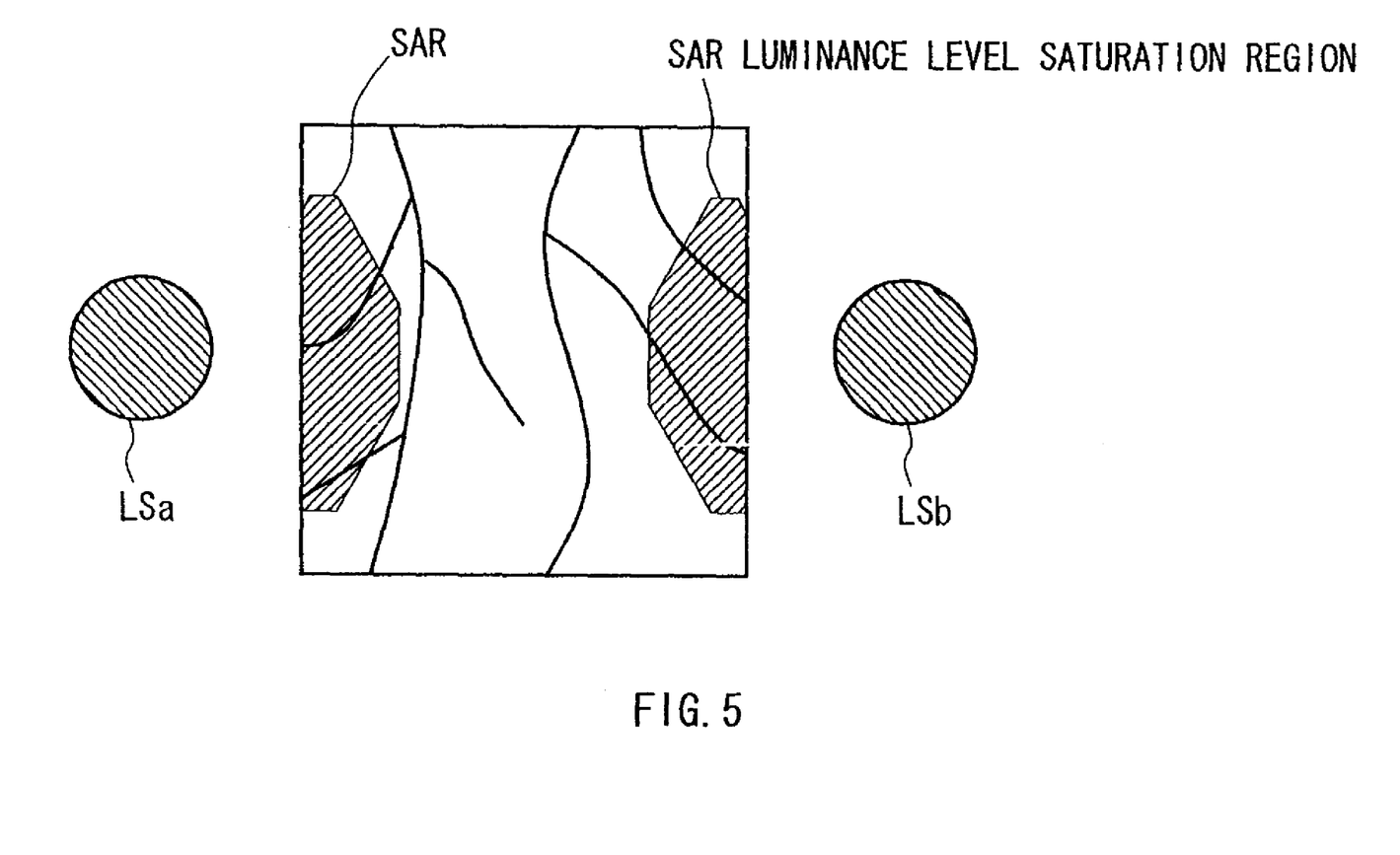
FIG. 5 is a schematic diagram explaining a luminance level saturation region.

Therefore, a charge signal of blood vessel light having a great light amount, specifically, as shown in FIG. 5, a charge signal of blood vessel pattern light of a part near the near-infrared light sources LSa and LSb may be saturated even if the signal is limited with the exposure time control process. In this case, the blood vessel image based on the digital blood vessel image signal D2 has unclear regions SAR having pseudo outlines due to the saturation. If this blood vessel image is used as identification information, the accuracy of the identification process deteriorates (hereinafter, such a region is called luminance level saturation region). Further, the luminance level saturation region SAR becomes apparent because individuals have different reflex pathways inside bodies and the light amount of blood vessel pattern light entering the CCD 11E through the body is also different.

Figure 6:
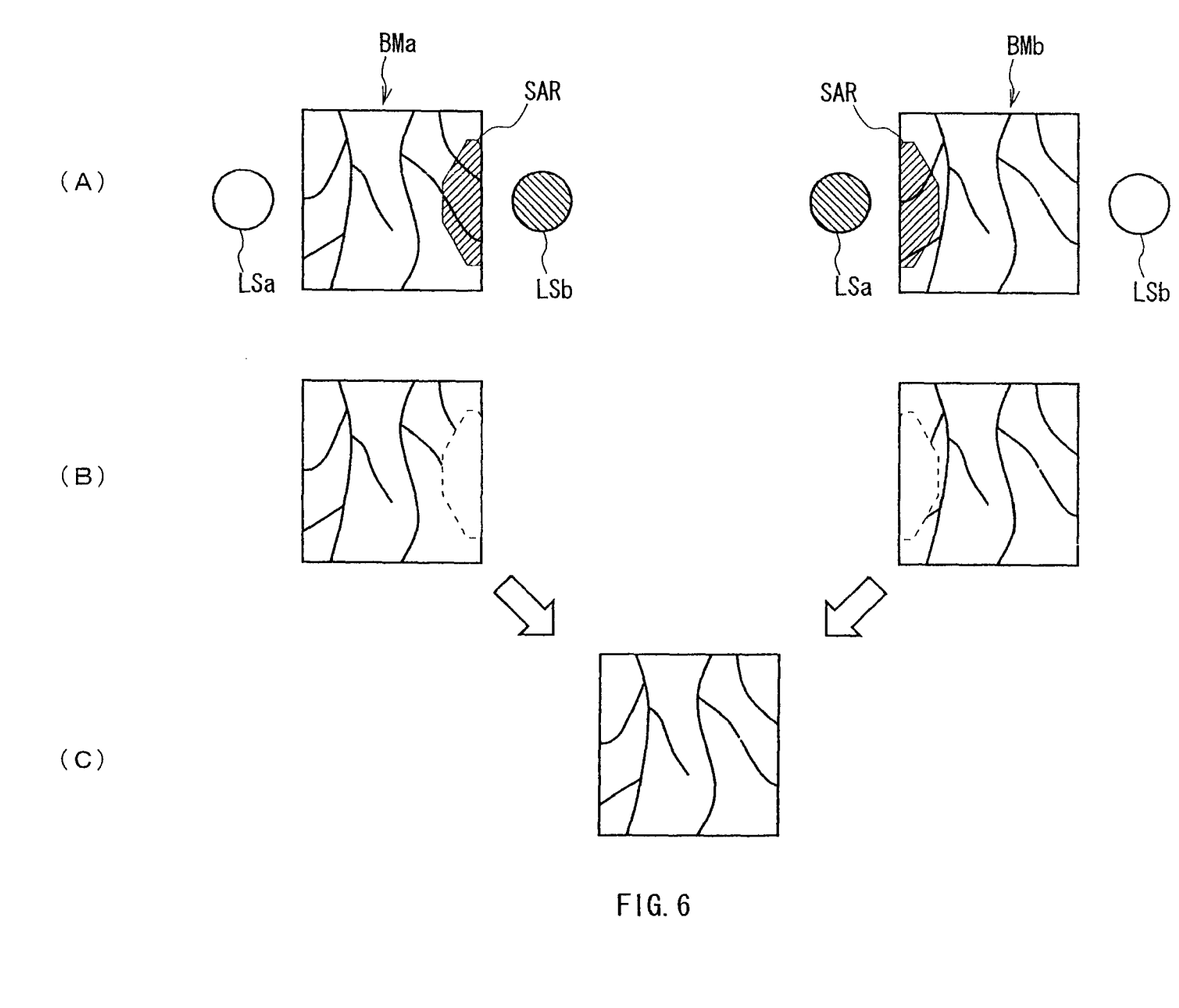
FIG. 6 is a schematic diagram explaining a blood vessel imaging control process according to the first embodiment.

Therefore, in the blood vessel imaging mode, as shown in FIG. 6, the imaging device 10 is designed to alternatively emit light from the near-infrared light sources LSa and LSb, and mask the luminance level saturation regions SAR included in the blood vessel images obtained via the CCD camera unit 11 and the A/D conversion unit 14.

Specifically, the light source control unit 21A of the blood vessel imaging control unit 21 alternatively set the near-infrared light sources LSa and LSb to ON/OFF every unit time. In this case, blood vessel pattern light (FIG. 6(A)) obtained through the finger FG from the near-infrared light source LSb is given to the data processing unit 15 as a digital blood vessel image signal D2 (FIG. 1) of a blood vessel image BMa having a luminance level saturation region SAR corresponding to a part near the near-infrared light source LSb.

Similarly, blood vessel pattern light (FIG. 6(A)) obtained through the finger FG from the near-infrared light source LSa is given to the data processing unit 15 as a digital blood vessel image signal D2 (FIG. 1) of a blood vessel image BMb having a luminance level saturation region SAR corresponding to a part near the near-infrared light source LSa.

The data processing unit 15 is designed to perform masking with the digital blood vessel image signal D2 of the blood vessel image BMa and the digital blood vessel image signal D2 of the blood vessel image BMa which are alternatively and sequentially given from the A/D conversion unit 14, as one unit. The data processing unit 15 masks the luminance level saturation regions SAR of the blood vessel images BMa and BMb of both digital blood vessel image signals D2 (FIG. 6(B)), and combines the blood vessel images BMa and BMb based on, for example, the blood vessel image BMa having the minimum ratio of the luminance level saturation region SAR to the entire image (FIG. 6(C)).

This composition result is a blood vessel image in which the luminance level saturation regions SAR of the blood vessel images BMa and BMb are supplemented by each other's corresponding good regions. Then the data processing unit 15 extracts a blood vessel formation pattern from the composition result, and stores and keeps the extracted unique blood vessel formation pattern in an internal memory (not shown).

By performing the image control process as described above, the imaging device 10 can eliminate the evenness of a blood vessel image caused due to a luminance level saturation region SAR, regardless of the positions of the near-infrared light sources LSa and LSb and individuals.

(1-2) Operations and Effects of the First Embodiment

According to the above configuration, the imaging device 10 alternatively irradiates a body with irradiation light of a luminance level higher than that in the air arriving at the body, from the near-infrared light sources LSa and LSb every unit time. Then the imaging device 10 electrically adjusts the imaging sensitivity of the CCD 11E which performs the photoelectric conversion on blood vessel pattern light obtained every unit time, masks the luminance level saturation regions SAR of the blood vessel images BMa and BMb (FIG. 6) based on the blood vessel pattern light, and composes the images with, for example, the blood vessel image BMa as a reference image.

Therefore, this imaging device 10 can eliminate the evenness of an image even if the image based on uneven blood vessel pattern light that is created because there is a difference in reflex pathway of near-infrared light inside a body depending on the positions of the light sources and individuals, thereby being capable of obtaining an even image representing the inside of the body regardless of the positions of the light sources and individuals.

According to the above configuration, a body is sequentially irradiated with irradiation light of a luminance level higher than that in the air arriving at the body, from the near-infrared light sources LSa and LSb every unit time, and the luminance level saturation regions SAR of the blood vessel images BMa and BMb obtained after the imaging sensitivity of the CCD 11E for performing the photoelectric conversion on blood vessel pattern light obtained through the inside of the body is electrically adjusted, and the images are combined, thereby being capable of creating an even image representing the inside of the body, regardless of the positions of the light sources and individuals and thus improving image quality.

(2) Second Embodiment

(2-1) Construction of Imaging Device

Figure 7:
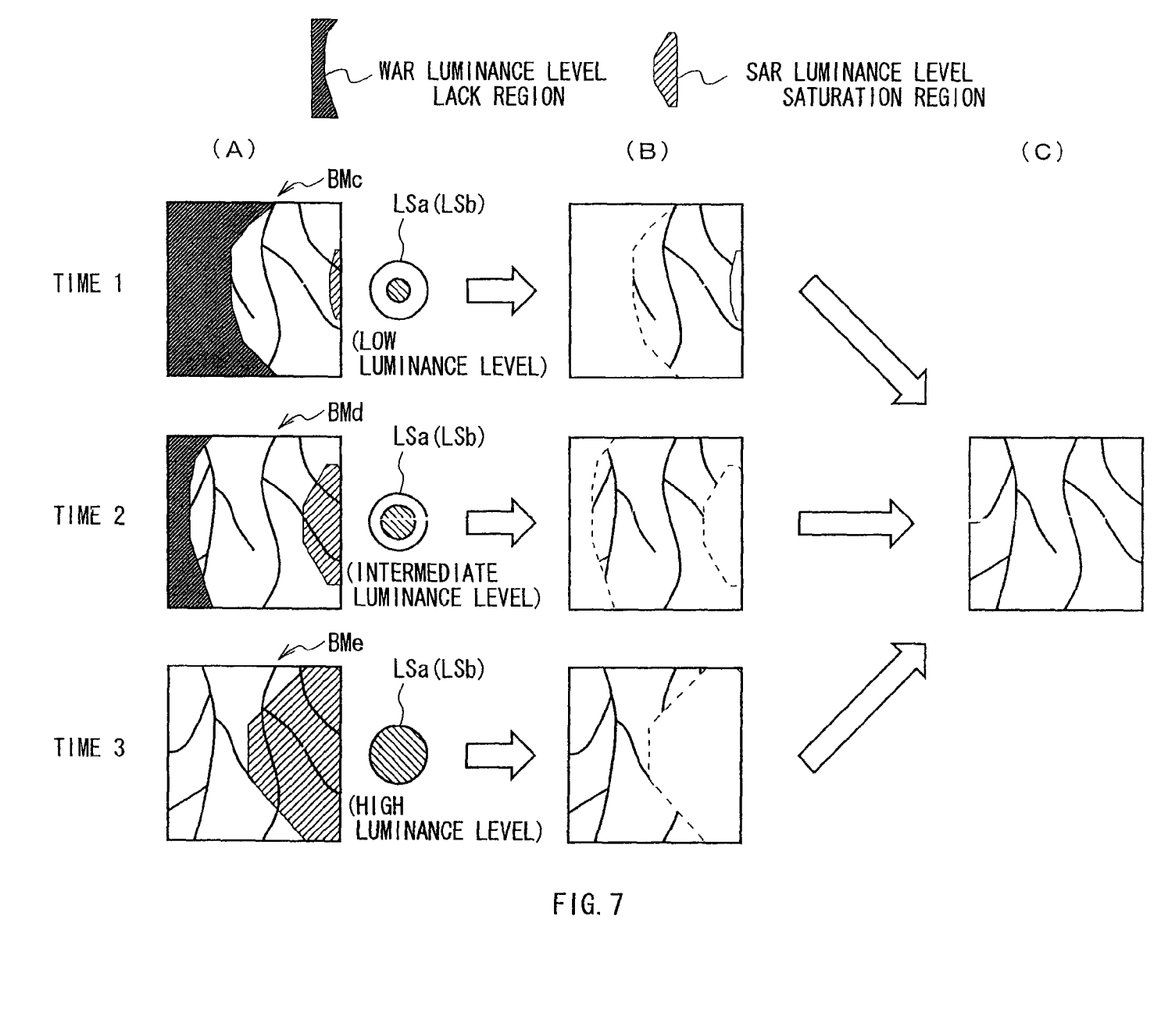
FIG. 7 is a schematic diagram explaining a blood vessel imaging control process according to the second embodiment.

There is different points from the first embodiment in that an imaging device 30 (FIG. 1) uses three kinds of luminance levels for near-infrared light in the blood vessel imaging mode as shown in FIG. 7, irradiates a finger FG with near-infrared light of the three kinds of luminance levels in order, from the near-infrared light sources LSa and LSb, and masks the luminance level saturation regions SAR and so on included in the blood vessel images sequentially obtained via the CCD camera unit 11 and the A/D conversion unit 14.

Specifically, a light source control unit 31A (FIG. 1) of a blood vessel imaging control unit 21 sequentially and variably controls output and so on to near-infrared light sources LS so that a luminance level higher than that of the outside light normally obtained in the air has a preset first, second or third value in order, and irradiates a finger FG with near-infrared light in the first luminance level state (hereinafter, referred to as low luminance level), a second luminance level state (hereinafter, referred to as intermediate luminance level), and a third luminance level state (hereinafter, referred to as high luminance level) in order, from the near-infrared light sources LS every unit time.

In a case of the low luminance level, the imaging sensitivity of the CCD 11E deteriorates because a light amount decreases as light is farther from the near-infrared light sources LSa and LSb. Therefore, blood vessel pattern light (FIG. 7(A)) obtained through the finger FG is given to a data processing unit 35 as a digital blood vessel image signal D2 (FIG. 1) of a blood vessel image BMc in which there is a large unclear region (hereinafter, referred to as luminance level lack region) having pseudo outlines according to the deterioration of the imaging sensitivity caused by the lack of light amount.

Similarly, in a case of the high luminance level, in contrast with the blood vessel pattern light obtained at the low luminance level, blood vessel pattern light obtained through the finger FG (FIG. 7(A)) is given to the data processing unit 35 as a digital blood vessel image signal D2 (FIG. 1) of a blood vessel image BMe in which a luminance level saturation region SAR becomes large as light is close to the near-infrared light sources LSa and LSb. In a case of the intermediate luminance level, blood vessel pattern light obtained through the finger FG is given to the data processing unit 35 (FIG. 1) as a digital blood vessel image signal D2 of a blood vessel image BMd having a luminance level lack region WAR and a luminance level saturation region SAR both in equal proportion.

Then the data processing unit 35 (FIG. 1) is designed to perform masking with the digital blood vessel image signals D2 of the blood vessel images BMc, BMd, and BMe given from the A/D conversion unit 14 as one unit. The data processing unit 35 masks the luminance level lack regions WAR and the luminance level saturation regions SAR of the blood vessel images BMc, BMd, and BMe (FIG. 7(B)).

Then the data processing unit 35 (FIG. 1) composes the blood vessel images BMc, BMd, and BMe obtained after the masking, based on, for example, the blood vessel image BMd having the minimum ratio of the luminance level lack region WAR and luminance level saturation region SAR to the entire image (FIG. 7(C)). This composition result is a blood vessel image in which the blood vessel images BMc, BMd, and BMe are supplemented by each other's good regions. Then the data processing unit 35 (FIG. 1) extracts a blood vessel formation pattern from the composition result, and stores and keeps the extracted unique blood vessel formation pattern in an internal memory (not shown).

As described above, the imaging device 30 (FIG. 1) performs the image control process, thereby being capable of eliminating the evenness of a blood vessel image due to a luminance level saturation region SAR, regardless of the positions of the near-infrared light sources LSa and LSb and individuals.

(2-2) Operations and Effects of the Second Embodiment

According to the above configuration, this imaging device 30 sequentially irradiates a body with irradiation light of three kinds of luminance levels higher than that in the air arriving at the body every unit time. Then the imaging device 30 electrically adjusts the imaging sensitivity of the CCD 11E for performing the photoelectric conversion on blood vessel pattern light obtained every unit time, masks the luminance level lack regions WAR and the luminance level saturation regions SAR of blood vessel images BMc, BMd, and BMe (FIG. 7)

based on the blood vessel pattern light and then composes the images with, for example, the blood vessel image BMd as a reference image.

Therefore, this imaging device 30 can eliminate the unevenness of an image even if the image based on uneven blood vessel pattern light is created because there is a difference in reflex pathway of near-infrared light inside a body depending on the positions of the light sources and individuals, thus being capable of obtaining an even image representing an inside of the body, regardless of the positions of the light sources and individuals.

In addition, this imaging device 30 can reduce driving power by an amount used for setting the near-infrared light sources LSa and LSb to ON/OFF (irradiation or non-irradiation of irradiation light). As a result, power consumption can be reduced as compared with the first embodiment.

According to the above configuration, a body is sequentially irradiated with irradiation light of three kinds of luminance levels higher than a luminance level of the air arriving at the body, every unit time, the luminance level lack regions WAR and the luminance level saturation region SAR of the blood vessel images BMc, BMd, and BMe obtained after the imaging sensitivity of the CCD 11 for performing the photoelectric conversion on blood vessel pattern light obtained through the inside of the body is electrically adjusted are masked, and then the images are composed, thereby being capable of reducing power consumption as compared with the first embodiment in which irradiation light is emitted and not emitted, as well as obtaining the same effects as the first embodiment.

(3) Third Embodiment

(3-1) Construction of Imaging Device

Figure 8:
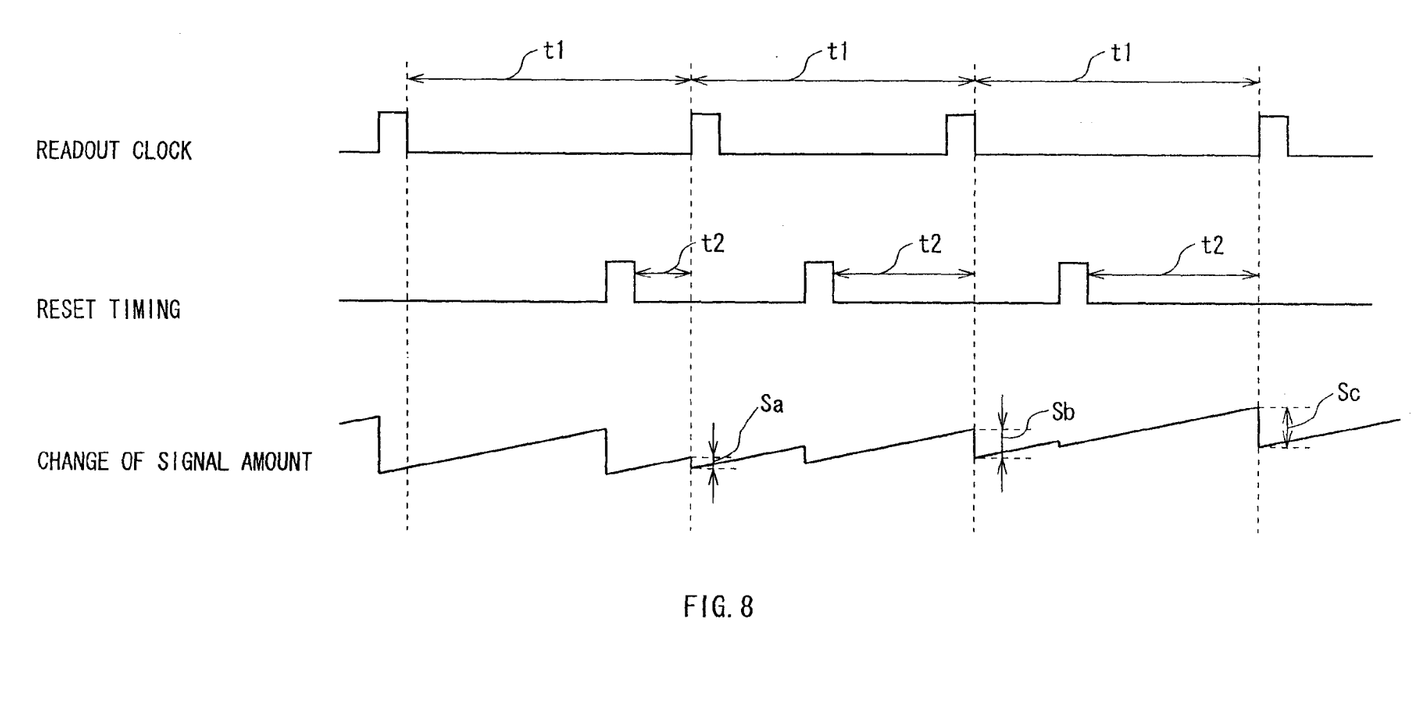
FIG. 8 is a schematic diagram showing an example of exposure time control.

There are different points from the first embodiment in that an imaging device 40 (FIG. 1) executes an exposure time control process so as to sequentially use three kinds of reset timing TM1, TM2, and TM3 which becomes faster in order every charge storage period t1 for the CCD 11E, as shown in FIG. 8, and masks luminance level lack regions WAR and luminance level saturation regions SAR included in blood vessel images obtained via the CCD 11E and the A/D conversion unit 14.

Specifically, a sensitivity adjustment unit 41B (FIG. 1) of a blood vessel imaging control unit 21 limits the amount of charge signal being accumulated in each photoelectric conversion element of the CCD 11E within the charge accumulation period t1 by sequentially performing resetting at the first, second and third reset timing TM1, TM2, and TM3. Then the CCD 11E reads the charge signals Sa, Sb, and Sc being accumulated after the amount of charge signal is limited with the exposure time control process of the sensitivity adjustment unit 41B (FIG. 1), as blood vessel image signals S2 (FIG. 1) at readout timing of a readout clock, and sends them to the A/D conversion unit 14.

Figure 9:
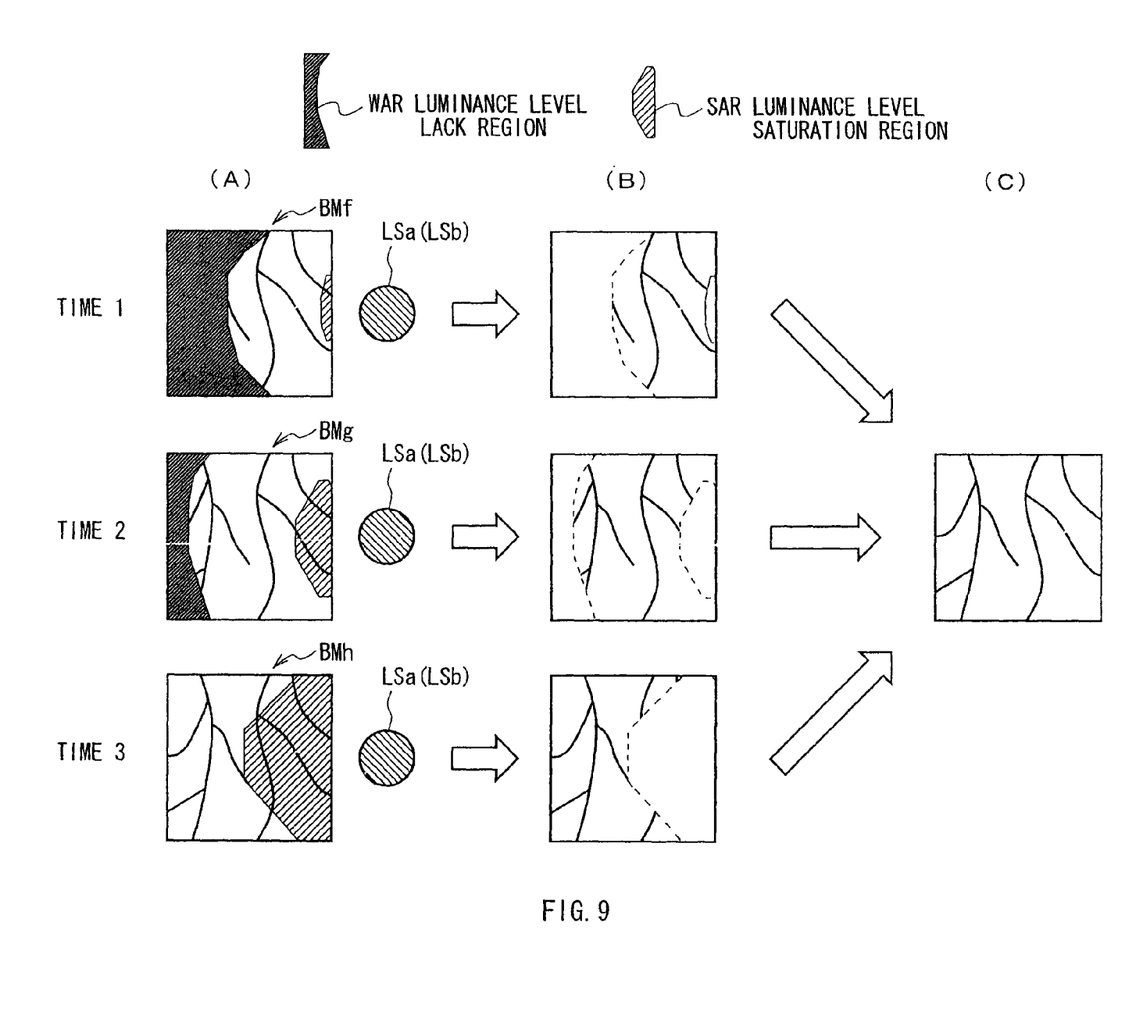
FIG. 9 is a schematic diagram explaining a blood vessel imaging control process according to the third embodiment.

In this case, as shown in FIG. 9, the blood vessel image signal S2 corresponding to the charge signal Sa is given to a data processing unit 45 as a digital blood vessel image signal D2 (FIG. 1) of a blood vessel image BMf in which a ratio of a luminance level lack region WAR to the entire image becomes high as the region is farther from the near-infrared light sources LSa and LSb because the imaging sensitivity deteriorates due to the shortest period (hereinafter, referred to as exposure period) t2 from the reset timing TM1 to readout timing.

Similarly, the blood vessel image signal S2 corresponding to the charge signal Sc is given to the data processing unit 45 as a digital blood vessel image signal D2 (FIG. 1) of a blood vessel image BMg in which a ratio of a luminance level saturation region SAR to the entire image becomes large as the region is close to the near-infrared light sources LSa and LSb because the imaging sensitivity is high due to the longest exposure period t2. The blood vessel image signal S2 corresponding to the charge signal Sb is given to the data processing unit 35 (FIG. 1) as a digital blood vessel image signal D2 of a blood vessel image BMh having a luminance level lack region WAR and a luminance level saturation region SAR both in equal proportion because the imaging sensitivity is middle due to an intermediate exposure period t2.

As described above, the sensitivity adjustment unit 41B (FIG. 1) executes the exposure time control process so as to sequentially use three kinds of reset timing TM1, TM2 and TM3 which becomes faster in order, every charge accumulation period t1 for the CCD 11E. Therefore, as described with reference to FIG. 7, blood vessel images BMf to BMh which are the same as those of the second embodiment in which a finger FG is sequentially irradiated with near-infrared light of three kinds of luminance levels in order can be obtained.

In this case, as in the case of the second embodiment, the data processing unit 45 masks the luminance level lack regions WAR and the luminance level saturation regions SAR of the blood vessel images BMf, BMg, and BMh by executing the masking process on the digital blood vessel image signals D2 of the blood vessel images BMf, BMg, and BMh given from the A/D conversion unit 14, and composes the resultant images, extracts a blood vessel formation pattern from the composition result, and stores and keeps the extracted unique blood vessel formation pattern in an internal memory (not shown).

As described above, the imaging device 40 performs the image control process, thereby being capable of eliminating the evenness of a blood vessel image corresponding to a luminance level saturation region SAR. regardless of the positions of the near-infrared light sources LSa and LSb and individuals.

(3-2) Operations and Effects of the Third Embodiment

According to the above configuration, this imaging device 40 irradiates a body with irradiation light of a luminance level higher than that in the air arriving at the body, adjusts the imaging sensitivity of the CCD 11E for performing the photoelectric conversion on blood vessel pattern light obtained through the inside of the body by sequentially changing the amount of charge signal being accumulated in the CCD 11E per charge accumulation period t1 (FIG. 8), masks the luminance level lack regions WAR and the luminance level saturation regions SAR of the images BMf, BMg and BMh (FIG. 9) based on the charge signals Sa, Sb and Sc obtained from the CCD 11E, and then composes the images.

Therefore, even if an image based on uneven blood vessel pattern light is obtained because there is a difference in reflex pathway of near-infrared light inside a body depending on the positions of the light sources and individuals, this imaging device 40 is capable of eliminating an evenness of the image, thereby being capable of obtaining an even image representing the inside of the body, regardless of the positions of the light sources and individuals.

In addition, this imaging device 40 is capable of obtaining an even image representing an inside of a body without variably controlling power or the like to the near-infrared light sources LSa and LSb, resulting in being capable of significantly reducing power consumption as compared with the first and second embodiments.

According to the above configuration, a body is irradiated with irradiation light of a luminance level higher than that in the air arriving at the body, the imaging sensitivity of the CCD 11E for performing the photoelectric conversion on blood vessel pattern light obtained through an inside of the body is adjusted by sequentially changing the amount of charge signal being accumulated in the CCD 11E per charge accumulation period t1 (FIG. 8), and the images BMf, BMg, and BMf (FIG. 9) based on the charge signals Sa, Sb, and Sc obtained from the CCD 11E are composed after their luminance level lack regions WAR and luminance level saturation regions SAR are masked, thereby being capable of significantly reducing power consumption as compared with the first and second embodiments because variable control of power to the near-infrared light sources LSa and LSb is not performed, as well as obtaining the same effects as the first and second embodiments.

(4) Other Embodiments

Figure 10:
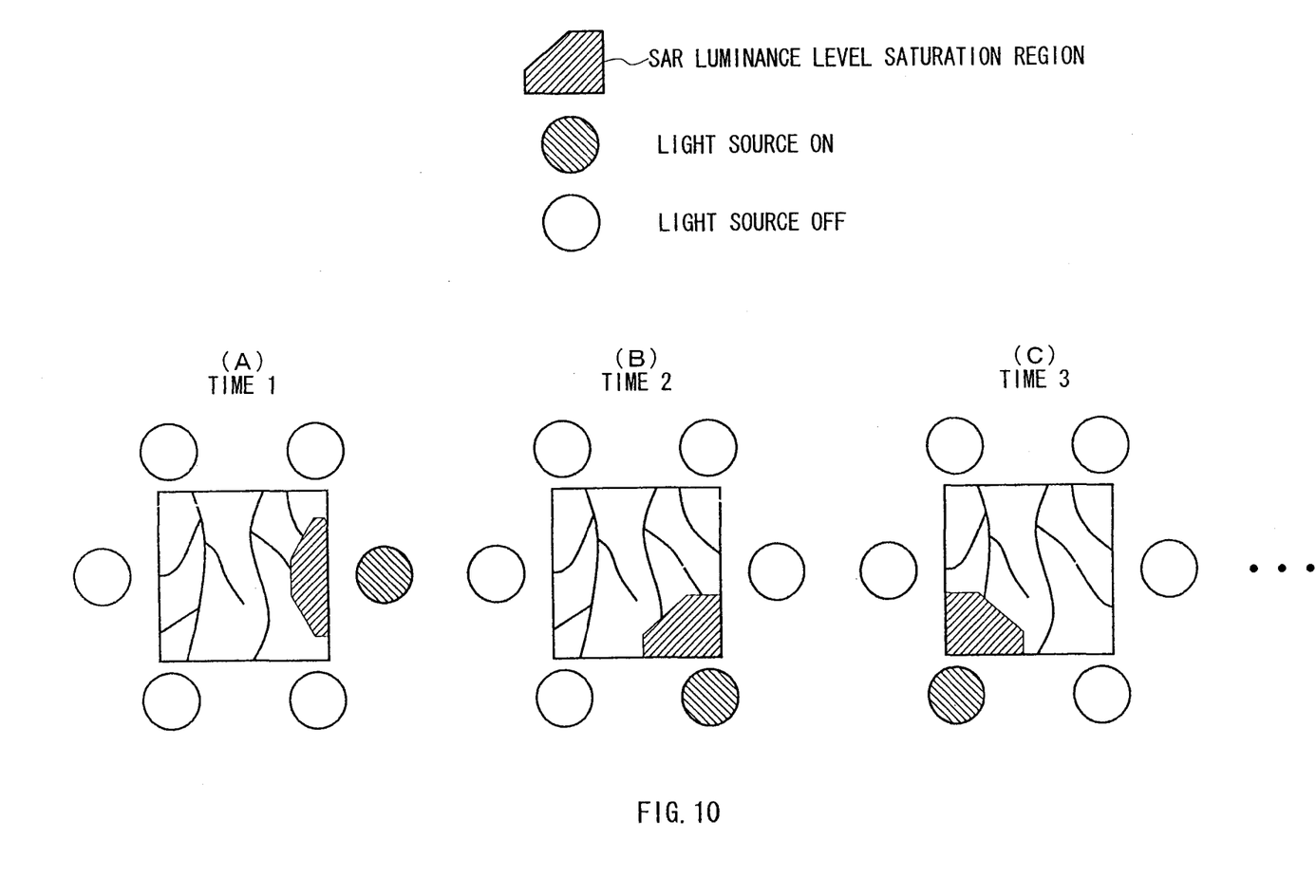
FIG. 10 is a schematic diagram explaining a blood vessel imaging control process according to another embodiment.

Note that the above first embodiment has described a case of sequentially and alternatively irradiating a body with irradiation light from the near-infrared light sources LSa and LSb every unit time. This invention, however, is not limited to this and, for example, as shown in FIG. 10, a plurality of near-infrared light sources can be arranged to sequentially irradiate the body with irradiation light from these near-infrared light sources in order. Alternatively, one movable near-infrared light source LSa can be provided to irradiate the body with irradiation light from different irradiation positions every unit time.

In this case, by performing masking with digital blood vessel image signals D2 of blood vessel images obtained from blood vessel pattern light obtained through the finger from the near-infrared light sources as one unit, a composed blood vessel image with high image quality can be obtained because many blood vessel images are used to be composed.

Further, in this case, near-infrared light is emitted with blood vessels inside a finger of a body as an irradiation target, and blood vessel pattern light obtained through the finger is imaged. This invention, however, is not limited to this and irradiation light which has a specificity for tissues can be emitted with tissues inside retina of a body or all body as an irradiation target and pattern scattered light obtained through the body can be imaged.

Further, in this case, the near-infrared light sources LS (LSa and LSb) are arranged in almost the same level as the positions of the CCD camera unit 11. This invention, however, is not limited to this and one or two or more near-infrared light sources can be arranged at other different positions. In this case, even if the positions of the light sources are changed, an even image representing an inside of a body can be obtained.

Furthermore, the above embodiment has described a case where, as a technique of the blood vessel imaging control unit 21 to control the light sources 21 and the CCD 11E corresponding to the light source control unit 21A (31A) and the sensitivity adjustment unit 21B (41B) of the blood vessel imaging control unit 21, in the first embodiment, a body is sequentially and alternatively irradiated with irradiation light of a luminance level higher than that in the air arriving at the body, from the near-infrared light sources LSa and LSb every unit time, and the imaging sensitivity of the CCD 11E for performing the photoelectric conversion on blood vessel pattern light obtained through the inside of the body is electrically adjusted. In the second embodiment, on the other hand, a body is sequentially irradiated with irradiation light of three kinds of luminance levels higher than that in the air arriving at the body in order every unit time, and the imaging sensitivity of the CCD 11E for performing the photoelectric conversion on blood vessel pattern light obtained through the inside of the body is electrically adjusted. In the third embodiment, a body is irradiated with irradiation light of a luminance level higher than that in the air arriving at the body, and the imaging sensitivity of the CCD 11E for performing the photoelectric conversion on blood vessel pattern light obtained through the inside of the body is adjusted by sequentially changing the amount of charge signal being accumulated in the CCD 11E within the charge accumulation period t1 (FIG. 8). This invention, however, is not limited to these and, when a body is sequentially irradiated with irradiation light of three kinds of luminance levels, resetting can be performed at reset timing which is associated with the luminance levels. Alternatively, other combinations can be applied.

Furthermore, the above embodiment has described a case of using the CCD 11E as a solid imaging element. This invention, however, is not limited to this and another solid imaging element such as a CMOS (ComplementSARy Metal Oxide Semiconductor) can be used.

Furthermore, the above embodiment has described a case where, as a masking means for masking luminance level deterioration regions (luminance level lack regions WAR and luminance level saturation regions SAR) of pattern images obtained from a solid imaging element and creating the masked images as images to be composed with a reference image, the data processing units 15, 35 and 45 for composing blood vessel images after masking their luminance level deterioration regions, and storing and keeping a unique blood vessel formation pattern extracted from the composition result in an internal memory (not shown) are applied. This invention, however, is not limited to this and a data processing unit for performing other processes can be applied for processes which are executed after the composition result is obtained.

Furthermore, the above embodiment has described a case where the light sources 21 and the CCD 11E are controlled by corresponding light source control unit 21A (31A), sensitivity control unit 21B (41B) and data processing unit 15 (35, 45). This invention, however, is not limited to this and a control process of each of the control units can be realized by programs.

Furthermore, the above embodiment has described a case where the mode switching unit 20 (FIG. 1) is applied as a mode switching means for driving an irradiation means and a sensitivity adjustment means according to switching to a mode to image pattern light out of a mode to image light in the air arriving from a subject and the mode to image pattern light. This invention, however, is not limited to this and only the mode to image pattern light can be executed.

INDUSTRIAL APPLICABILITY

This invention can be used for a case of imaging blood vessels inside a body.

EXPLANATION OF REFERENCE NUMERALS 10, 30, 40 . . . IMAGING DEVICE, 11 . . . CCD CAMERA UNIT, 11E . . . COD, 12 . . . MCU, 15 . . . DATA PROCESSING UNIT, 20 . . . MODE SWITCHING UNIT, 21, 31, 41 . . . BLOOD VESSEL CONTROL

UNIT, 21A, 31A . . . LIGHT SOURCE CONTROL UNIT, 21B, 41B . . . SENSITIVITY ADJUSTMENT UNIT

The invention claimed is:

1. An imaging device comprising:
an ambient light measurement receiving unit configured to receive a measurement of a luminance level of light in the air arriving at a body;
a light source control unit configured to control light sources to irradiate the body with irradiation light of a luminance level greater than the measurement of the luminance level of air surrounding the body;
an imaging element configured to perform photoelectric conversion on a pattern of light scattered through an inside of the body;
a sensitivity adjustment unit configured to adjust imaging sensitivity of the imaging element; and
an image generating unit configured to generate an image that excludes luminance level deterioration regions by replacing the luminance level deterioration regions with a reference image generated at a different sensitivity.

2. The imaging device according to claim 1, wherein:
the light source control unit is configured to control the light sources so as to sequentially irradiate the body with irradiation light every unit time; and
the image generating unit is configured to remove the luminance level deterioration regions from the image every unit time and to compose the image with the reference image.

3. The imaging device according to claim 1, wherein:
the light source control unit is configured to control the light sources so as to sequentially irradiate the body every unit time at luminance levels different from each other; and
the image generating unit is configured to remove the luminance level deterioration region of the image every unit time and compose the image with the reference image.

4. The imaging device according to claim 1, wherein:
the sensitivity adjustment unit is configured to adjust the imaging sensitivity by sequentially changing an amount of charge signal accumulated in the imaging element as a result of the photoelectric conversion for each unit time; and
the image generating unit is configured to remove the luminance level deterioration region of the image based on the amount of charge obtained from the imaging element and to compose the image with the reference image.

\* \* \* \* \*